(12) United States Patent
Juhasz et al.

(10) Patent No.: US 6,623,476 B2
(45) Date of Patent: *Sep. 23, 2003

(54) DEVICE AND METHOD FOR REDUCING CORNEAL INDUCED ABERRATIONS DURING OPHTHALMIC LASER SURGERY

(75) Inventors: Tibor Juhasz, Irvine, CA (US); Ronald M. Kurtz, Irvine, CA (US); Carlos G. Suarez, Irvine, CA (US)

(73) Assignee: IntraLase Corp., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/834,979

(22) Filed: Apr. 13, 2001

(65) Prior Publication Data

US 2001/0021844 A1 Sep. 13, 2001

Related U.S. Application Data

(63) Continuation-in-part of application No. 09/172,819, filed on Oct. 15, 1998, now Pat. No. 6,254,595.

(51) Int. Cl.[7] .............................................. A61B 18/20
(52) U.S. Cl. ............................................. 606/5; 606/17
(58) Field of Search .............................. 606/1, 4, 5, 17; 607/80, 88, 89; 359/700

(56) References Cited

U.S. PATENT DOCUMENTS

| 4,573,778 A | | 3/1986 | Shapiro |
| 4,891,043 A | | 1/1990 | Zeimer et al. |
| 4,903,695 A | | 2/1990 | Warner et al. |
| 4,994,058 A | | 2/1991 | Raven et al. |
| 5,226,903 A | | 7/1993 | Mizuno |
| 5,549,632 A | * | 8/1996 | Lai ................................ 606/5 |
| 5,817,115 A | * | 10/1998 | Nigam ........................ 606/166 |
| 6,126,668 A | * | 10/2000 | Bair et al. ................... 606/166 |
| 6,254,595 B1 | * | 7/2001 | Juhasz et al. .................. 606/17 |
| 6,325,792 B1 | * | 12/2001 | Swinger et al. ............... 606/11 |
| 6,342,053 B1 | | 1/2002 | Berry |

FOREIGN PATENT DOCUMENTS

| WO | 9409849 | * | 5/1994 |
| WO | 9515134 | * | 6/1995 |

* cited by examiner

*Primary Examiner*—Lee Cohen
(74) *Attorney, Agent, or Firm*—Fulbright & Jaworski LLP

(57) ABSTRACT

A disposable lens for reconfiguring the cornea of an eye for ophthalmic laser surgery includes a lens which has a flat anterior surface that is formed opposite a contact surface. A skirt surrounds the contact surface and extends outwardly therefrom to define a chamber. The skirt is formed with a groove which creates a suction channel between the skirt and the contact surface in the chamber. In its operation, the lens is positioned over the cornea and a vacuum pump is selectively activated to create a partial vacuum in the suction channel. Due to this partial vacuum, the cornea is drawn into the chamber where it is urged against the contact surface of the lens. The result of this is that the cornea is flattened into a configuration where the introduction of spherical aberration and coma into a light beam passing into the cornea is reduced or eliminated.

37 Claims, 3 Drawing Sheets

DEVICE AND METHOD FOR REDUCING CORNEAL INDUCED ABERRATIONS DURING OPHTHALMIC LASER SURGERY

This application is a continuation-in-part of application Ser. No. 09/172,819, filed Oct. 15, 1998, now U.S. Pat. No. 6,254,595. The contents of application Ser. No. 09/172,819 are incorporated herein by reference.

FIELD OF THE INVENTION

The present invention pertains generally to surgical devices. More particularly, the present invention pertains to surgical lenses which are used in ophthalmic laser surgery. The present invention is particularly, but not exclusively, useful as a lens for temporarily reconfiguring the cornea from an imperfect shape which causes light passing through the cornea to experience aberration into a shape that allows light to pass through the cornea with little or no aberration.

BACKGROUND OF THE INVENTION

For ophthalmic laser procedures involving the photodisruption of eye tissue, it is extremely important for the laser beam to be properly focused to a spot at a prescribed location inside the tissue. To make accurate incisions with the laser, it is extremely important that the focal spot have good definition. Specifically, it is desirable that the laser beam reach the focal spot free from aberrations that can distort the definition of the focal spot.

For ophthalmic laser procedures involving the cornea, a beam of laser light is generally passed through the anterior surface of the cornea and focused within the cornea. Unfortunately, since the anterior surface of the cornea in its natural state is nearly spherical, once a beam of light passes through the anterior surface of the cornea, aberrations are introduced into the beam that cause the beam to distort. For light beams that are focused to a focal spot within the cornea, these corneal induced aberrations distort the definition of the focal spot. It follows that more accurate incisions can be performed by reducing or eliminating these corneal induced aberrations.

For light beams that are focused to a focal spot within the cornea, both spherical aberration and coma cause a loss of definition of the focal spot. Conversely, it is known that when a light beam passes through a flat interface between two mediums, no spherical aberration or coma is introduced into the beam. Similarly, when a light beam passes through a nearly flat or slightly curved interface between two mediums, the effects of spherical aberration and coma are much less pronounced than for a light beam passing through a nearly spherical interface, such as the anterior surface of the cornea. As recognized by the present invention, the effects of spherical aberration and coma on light beams passing through the anterior surface of the cornea can be reduced or eliminated by reconfiguring the anterior surface of the cornea from its nearly spherical natural shape to a flatter configuration.

Generally, no two corneas are identical. Rather, the exact shape and curvature of the anterior shape of each cornea is slightly different. Consequently, each cornea in its natural state introduces different amounts of aberration into a light beam passing through the anterior surface of the cornea. For a light beam focused to a focal spot within the cornea, the unique shape of each cornea effects the definition of the focal spot differently. The present invention recognizes that the effects of spherical aberration and coma on light beams passing through the anterior surface of the cornea can be predicted by flattening the anterior surface of the cornea against a surface of known curvature. By using a surface of known curvature, a focal spot of known definition can be obtained and this knowledge can be used to ensure the desired surgical effect.

In light of the above, it is an object of the present invention to provide a disposable lens which will reconfigure the cornea for surgical laser procedures into a configuration wherein the effects of spherical aberration and coma on a light beam passing through the anterior surface of the cornea are reduced or eliminated. Yet another object of the present invention is to provide a disposable lens which will stabilize and maintain a proper orientation of the eye during ophthalmic laser surgery. Still another object of the present invention is to provide a disposable lens which will beneficially maintain near-normal intraocular pressure during ophthalmic laser surgery. Another object of the present invention is to provide a disposable lens which is easy to use, relatively simple to manufacture and comparatively cost effective.

SUMMARY OF THE INVENTION

In one embodiment for the present invention, a lens for use in ophthalmic laser surgery includes an optical element in combination with a suction means. More specifically, the suction means is connected in fluid communication with the optical element to selectively create a partial vacuum between the optical element and the cornea when the lens is positioned over an eye. In response to the partial vacuum, the cornea is forced against the optical element. This reconfigures the cornea for laser surgery and thereby reduces or eliminates optical aberrations that would otherwise be caused by the natural shape of the cornea.

In more detail, the optical element of the present invention includes a lens member which has two opposed surfaces; a substantially flat anterior surface and a substantially flat or slightly curved contact surface. Specifically, as intended for the present invention, the contact surface can be shaped flat or slightly curved to cause the shape of the anterior surface of the cornea to change when the anterior surface of the cornea is held against the contact surface. Preferably, the lens member is made of a substantially clear, medical grade plastic. Additionally, a skirt surrounds the contact surface and extends outwardly therefrom to establish and surround a recessed chamber and define an opening to the recessed chamber. In the preferred embodiment, the skirt is formed with a sealing surface for contacting the cornea. The sealing surface of the skirt is preferably formed having a concave shape extending into the recess. The concave shape of the sealing surface allows the skirt to establish a seal with the cornea when the lens is placed against the eye. Preferably, the sealing surface of the skirt is made of a soft medical grade plastic to further facilitate a strong seal between the skirt and the cornea during use. Inside the recessed chamber, a suction channel is provided at the interface between the contact surface and the skirt.

A suction device, such as a vacuum pump or a syringe, is connected in fluid communication with the recessed chamber via the suction channel. With this combination, a partial vacuum can be created in the recessed chamber whenever the opening to the chamber is covered. Specifically, as intended for the present invention, the opening to the chamber is to be covered by the cornea, and the cornea is to be drawn into the chamber where it is flattened against the contact surface of the lens.

As intended for the present invention, the lens can be mounted on a retainer ring which is attached to the laser system that is being used. More specifically, the retainer ring holds the lens in a predetermined orientation relative to the laser system so that the laser surgery can be performed.

In the operation of the present invention, the aplanatic lens is positioned over the eye so that the cornea of the eye is covered by the opening into the recessed chamber. The suction device is then activated to create a partial vacuum in the chamber. Due to this partial vacuum, the cornea is pulled or drawn into the chamber. Specifically, the cornea is flattened against the contact surface of the optical element. As indicated above, with the flattening of the cornea, spherical aberrations and comas which would otherwise be caused by the spherical geometry of the cornea are reduced or eliminated. After the particular ophthalmic laser procedure has been completed, the suction device is deactivated, the partial vacuum is dissipated, and the aplanatic lens is removed from the eye. The lens can be discarded and another new aplanatic lens may be used for the next patient.

In another embodiment for the present invention, the lens member as described above can be used in conjunction with a skirt formed with projections for holding the skirt and lens member in position relative to the eye. In this embodiment, the skirt surrounds the contact surface of the lens member and extends outwardly therefrom to establish and surround a recessed chamber and define an opening for the chamber. A plurality of projections are provided extending from the skirt near the opening for engagement with the cornea. A mechanism is provided to attach the lens member and skirt to a laser source.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
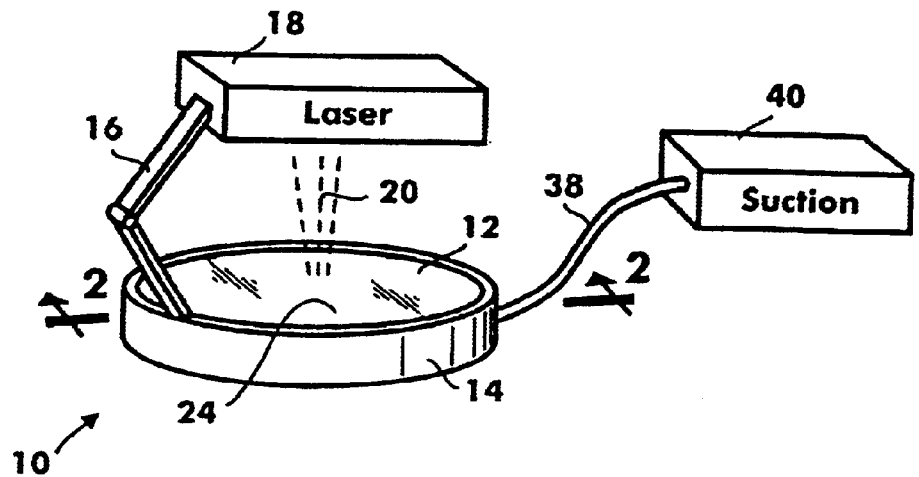
FIG. 1 is a perspective view of a lens in accordance with the present invention shown with accompanying components.

Referring initially to FIG. 1, a lens system in accordance with the present invention is shown and generally designated 10. As shown, the system 10 includes a lens member 12 which is mounted on a retainer ring 14. Further, the retainer ring 14 is adjustably connected via an extension arm 16 to a laser source 18. For purposes of the present invention, the laser source 18 is activated to generate a laser beam 20 which is directed through the lens member 12. As will become more apparent with further disclosure, the lens member 12 is configured to eliminate, or substantially reduce any spherical aberration or coma that may otherwise have been caused by the spherical nature of the cornea 22 of an eye.

Figure 2:
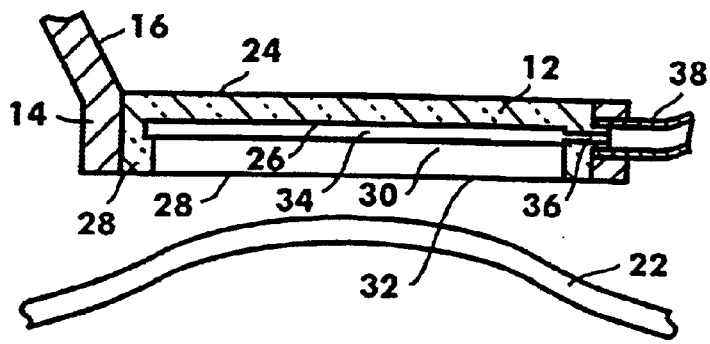
FIG. 2 is a cross-section view of a lens in accordance with the present invention as seen along the line 2—2 in FIG. 1 in position for engagement with the cornea of an eye.

The actual structure of the lens member 12 will perhaps be best appreciated by reference to FIG. 2 wherein it will be seen that the lens member 12 is formed with an anterior surface 24 and a contact surface 26. It is to be appreciated that the anterior surface 24 can be substantially flat. Likewise, the contact surface 26 can be substantially flat, as shown in FIG. 2. Further, the contact surface 26 can be substantially parallel to the anterior surface 24. In FIG. 2 it will also be seen that the lens member 12 is formed with a skirt 28. Specifically, the skirt 28 extends outwardly from the contact surface 26, as shown, and surrounds the contact surface 26 to create a recessed chamber 30.

Still referring to FIG. 2, it will be seen that the skirt 28 of lens member 12 establishes an opening 32 into the recessed chamber 30. Further, the lens member 12 of the present invention is formed with a suction channel 34 which surrounds the contact surface 26, and which is located between the skirt 28 and the contact surface 26. As shown, the suction channel 34 is open along its length for fluid communication with the recessed chamber 30. FIG. 2 also shows that an air passageway 36 is formed through the skirt 28 for fluid communication therethrough between a tube 38 and the suction channel 34. Consequently, tube 38 is in also in fluid communication with the recessed chamber 30. As shown in FIG. 1, a suction device 40, such as a vacuum pump, is connected with the tube 38 so that with activation of the suction device 40, a partial vacuum can be created in the recessed chamber 30 of the lens member 12.

Figure 3:
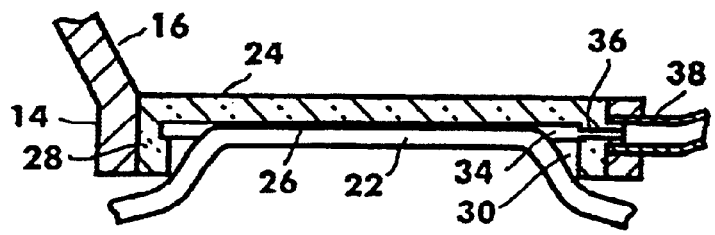
FIG. 3 is a cross-section view of the lens shown in FIG. 2 engaged with the cornea of an eye.

The operation of the lens system 10 shown in FIG. 2 can best be appreciated by cross referencing FIGS. 2 and 3. First, the lens member 12 is positioned above the cornea 22 of an eye substantially as shown in FIG. 2. The lens member 12 is then lowered into contact with the exterior surface of the eye (i.e. the cornea, limbus and/or sclera) until the skirt 28 comes into contact with the exterior surface of the eye. Preferably, at this point the cornea 22 completely covers the opening 32 into the recessed chamber 30. With the lens member 12 positioned on the cornea 22 as described, the suction device 40 is activated to create a partial vacuum in the recessed chamber 30. Due to the partial vacuum that is created by the suction device 40 in the recessed chamber 30, the cornea 22 is drawn or pulled into the recessed chamber 30 substantially as shown in FIG. 3. Specifically, the cornea 22 is allowed to be pulled into the recessed chamber 30 until the cornea 22 has been flattened against the contact surface 26 of the lens member 12. With this configuration for the cornea 22, i.e. when the cornea 22 has been somewhat flattened against the contact surface 26, the laser beam 20 from laser source 18 will be essentially free from the spherical aberrations and coma which would otherwise be caused by the cornea 22.

Figure 4:
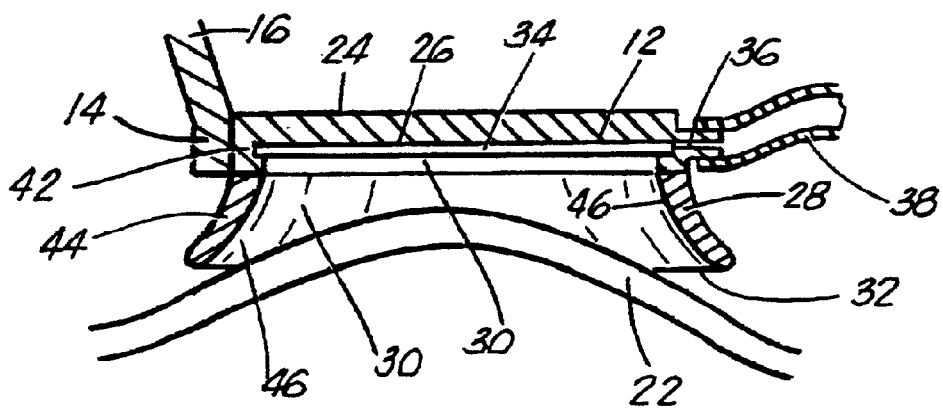
FIG. 4 is a cross-section view of a lens in accordance with the present invention having an extended skirt, shown in position for engagement with the cornea of an eye.

FIG. 4 shows another embodiment of a lens 12 in accordance with the present invention. As shown, in this embodiment, the skirt 28 is extended and includes a ring portion 42 and an extension 44. As shown, the extension 44 is attached to the ring portion 42 and projects therefrom. Also shown, the skirt 28 surrounds a recessed chamber 30 and establishes an opening 32 to the recessed chamber 30. The extension 44 of the skirt 28 is formed with a sealing surface 46. As shown, the sealing surface 46 is preferably formed having a concave curvature extending into the recessed chamber 30. This concave curvature facilitates a tight seal between the exterior surface of the eye and the skirt 28 during use.

Figure 5:
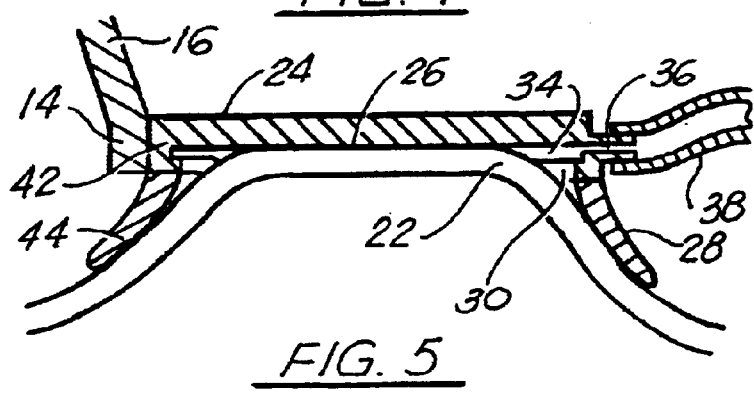
FIG. 5 is a cross-section view of the lens shown in FIG. 4 engaged with the cornea of an eye.

The operation of the lens 12 shown in FIG. 4 can best be appreciated by cross referencing FIGS. 4 and 5. First, the lens member 12 is positioned above the cornea 22 of an eye substantially as shown in FIG. 4. The lens member 12 is then lowered into contact with the exterior surface of the eye until the sealing surface 46 of the skirt 28 comes into contact with the exterior surface of the eye. At this point the cornea 22 completely covers the opening into the recessed chamber 30. With the lens member 12 positioned on the cornea 22 as described, the suction device 40 is activated to create a partial vacuum in the recessed chamber 30. Due to the partial vacuum that is created by the suction device 40 in the recessed chamber 30, the cornea 22 is drawn or pulled into the recessed chamber 30 substantially as shown in FIG. 5. Specifically, the cornea 22 is allowed to be pulled into the recessed chamber 30 until the cornea 22 has been flattened against the contact surface 26 of the lens member 12. With this configuration for the cornea 22, i.e. when the cornea 22 has been substantially flattened against the contact surface 26, less spherical aberration and coma will be introduced into a light beam passing into the reconfigured cornea 22 than would be introduced into an identical light beam passing into a cornea 22 that is not reconfigured.

Figure 6:
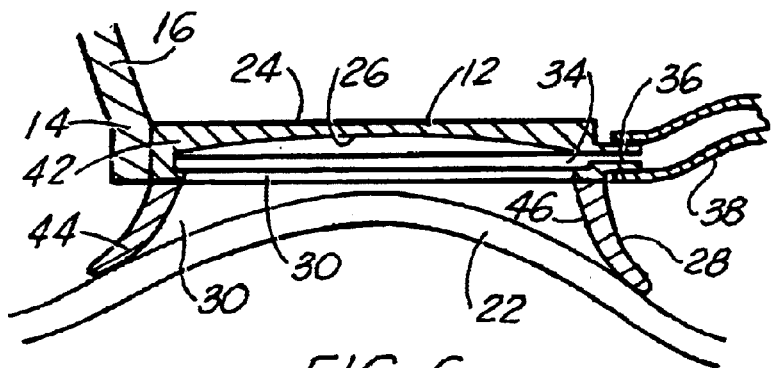
FIG. 6 is a cross-section view of a lens in accordance with the present invention having an extended skirt and a slightly curved contact surface, shown in position for engagement with the cornea of an eye.
Figure 7:
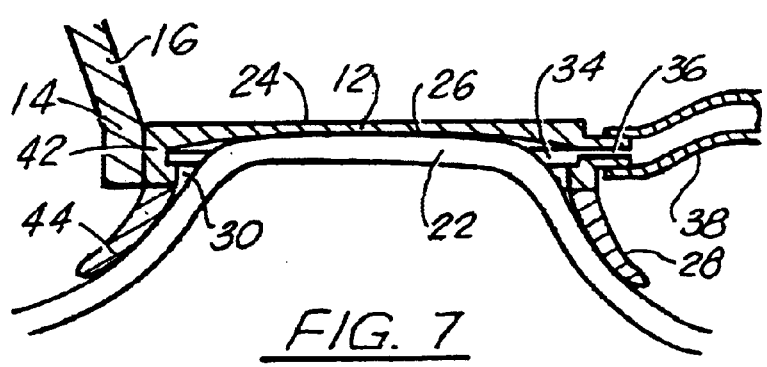
FIG. 7 is a cross-section view of the lens shown in FIG. 6 engaged with the cornea of an eye.

FIGS. 6 and 7 show another embodiment of a lens 12 in accordance with the present invention. As shown, in this embodiment, the contact surface 26 is slightly curved. Although the substantially flat contact surface 26 shown in FIG. 2 provides an interface with the cornea 22 that introduces little or no spherical aberration and coma into a light beam passing through the interface, the slightly curved contact surface 26 shown in FIGS. 6 and 7 greatly reduces spherical aberration and coma, and does so at a reduced intraocular pressure. Stated differently, reconfiguring the cornea 22 against a substantially flat contact surface 26 results in a slightly higher intraocular pressure than reconfiguring the cornea 22 against a slightly curved contact surface 26. As can be seen by cross referencing FIGS. 6 and 7, the cornea 22 has a substantially flatter curvature after reconfiguration against the slightly curved contact surface 26 (FIG. 7) than before reconfiguration (FIG. 6). Further, since the contact surface 26 in this embodiment is only slightly curved, when suction is applied at passageway 36 adjacent to the slightly curved contact surface 26, the cornea 22 is still drawn into the recessed chamber 30 and flattened against the slightly curved contact surface 26.

Figure 8:
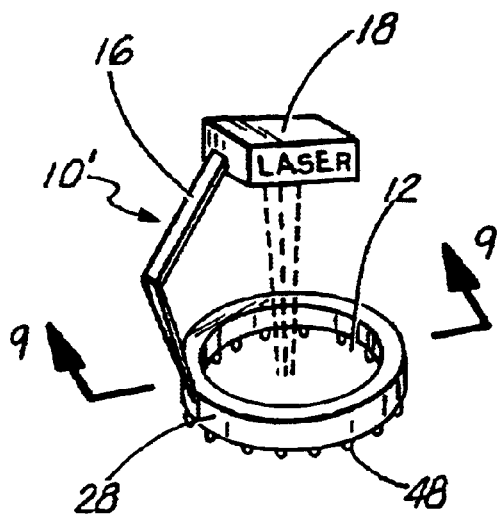
FIG. 8 is perspective view of another embodiment of a lens in accordance with the present invention shown with accompanying components.
Figure 9:
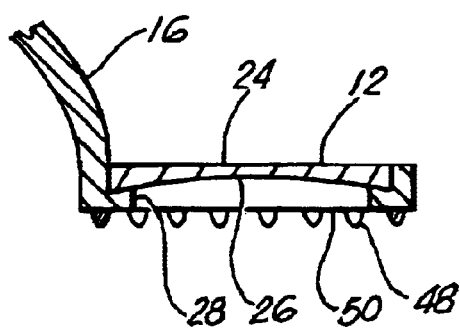
FIG. 9 is a cross-section view of a lens embodiment shown in FIG. 8 as seen along the line 9—9 in FIG. 8.
Figure 10:
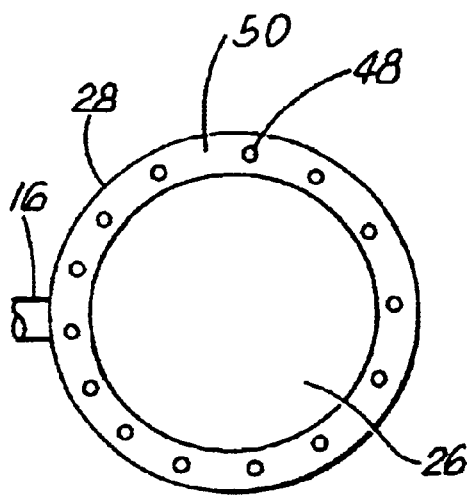
FIG. 10 is a bottom plan view of a lens embodiment shown in FIG. 8.
Figure 11:
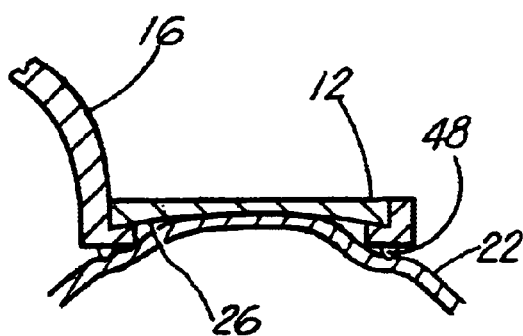
FIG. 11 is a cross-section view of the lens shown in FIG. 8 engaged with the cornea of an eye.

Referring now to FIG. 8, another embodiment of the lens system in accordance with the present invention is shown and designated 10'. In this embodiment, the lens member 12 includes a skirt 28 formed with projections 48. As shown with cross reference to FIGS. 9 and 10, the skirt 28 is formed with an annular surface 50. As further shown, the plurality of projections 48 are preferably distributed around the circumference of the skirt 28, with each projection 48 extending from the annular surface 50 of the skirt 28. Referring now to FIG. 11, the lens member 12 is shown after being pressed onto the eye to reconfigure the cornea 22 against the contact surface 26. As shown, the projections 48 are provided to engage the cornea 22 and prevent the cornea 22 from moving relative the lens member 12.

While the particular invention as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for reconfiguring the anterior surface of a cornea of an eye for ophthalmic laser surgery which comprises:

an optical element having an anterior side and a posterior side, said posterior side being formed with a recessed chamber and having a contact surface and a sealing surface; and a suction device connected in fluid communication with said recessed chamber to draw the cornea into the chamber and reconfigure the cornea against said contact surface when said sealing surface is pressed against the exterior of the eye.

2. A device as recited in claim 1 wherein said contact surface is substantially flat.

3. A device as recited in claim 1 wherein said contact surface is curved.

4. A device as recited in claim 1 wherein said sealing surface is concave extending into said recessed chamber and formed of a soft, medical grade plastic.

5. A device as recited in claim 1 wherein said posterior side is formed with a groove adjacent to said contact surface, and further comprising a passageway having a first end in contact with said groove and a second end in fluid communication with said suction device, said groove for transmitting a suction force to said contact surface to reconfigure the cornea and hold the reconfigured cornea against the contact surface during ophthalmic laser surgery.

6. A device as recited in claim 1 further comprising a retainer ring, said optical element being mounted on said retainer ring and further, wherein said retainer ring is attached to a laser system.

7. A device as recited in claim 1 wherein said contact surface is transparent.

8. A device as recited in claim 1, wherein said suction device is selected from the group of suction devices consisting of: a vacuum pump, a syringe, and a device that creates a partial vacuum.

9. A device as recited in claim 1, wherein said suction device is a device that creates a partial vacuum.

10. A method for ophthalmic laser surgery which comprises the steps of:

providing a lens having a lens member, said lens member formed with an anterior surface and a contact surface, said contact surface being opposed to said anterior surface, said lens having a skirt surrounding said contact surface and extending outwardly therefrom to define a recessed chamber therebetween, said skirt having a sealing surface, and said lens further having a suction device in fluid communication with said recessed chamber for creating a partial vacuum therein between said contact surface and a cornea;

placing said sealing surface of said skirt against the exterior surface of an eye;

creating a partial vacuum in said recessed chamber with said suction device to draw the cornea into said recessed chamber and reconfigure the cornea against said contact surface; and passing a laser beam through said anterior surface and said contact surface and into the cornea to perform ophthalmic laser surgery.

11. A method as recited in claim 10 wherein said contact surface is substantially flat.

12. A method as recited in claim 10 wherein said contact surface is curved.

13. A method as recited in claim 10 wherein said sealing surface is concave extending into said recessed chamber and formed of a soft, medical grade plastic.

14. A method as recited in claim 10 wherein said contact surface is shaped to introduce less spherical aberration to said laser beam as said laser beam passes into the reconfigured cornea than is introduced into an identical laser beam passing into a cornea that is not reconfigured.

15. A method as recited in claim 10 wherein said lens member is transparent.

16. A method as recited in claim 10, wherein said suction device is selected from the group of suction devices consisting of: a vacuum pump, a syringe, and a device that creates a partial vacuum.

17. A method as recited in claim 10, wherein said suction device is a device that creates a partial vacuum.

18. A lens system for reconfiguring a cornea and holding the reconfigured cornea during a laser treatment, said system comprising:

a lens member having an anterior surface and formed with a contact surface opposed to said anterior surface, said contact surface shaped to reconfigure the cornea;

a skirt, said skirt having a sealing surface and said skirt surrounding said contact surface and projecting outwardly therefrom to define a recessed chamber therebetween, said recessed chamber having an opening; and a passageway positioned substantially adjacent to said contact surface, said passageway in fluid communication with said recessed chamber; and a suction device in fluid communication with said passageway for creating a partial vacuum in said recessed chamber to reconfigure the cornea against said contact surface when said cornea is placed over said opening of said recessed chamber.

19. A lens system as recited in claim 18 further comprising:

a means for mounting said lens member and said skirt to a laser system.

20. A lens system as recited in claim 18 further comprising:

a laser source for producing a laser beam, said laser source positioned to pass said laser beam through said lens member.

21. A lens system as recited in claim 18, wherein said suction device is selected from the group of suction devices consisting of: a vacuum pump, a syringe, and a device that creates a partial vacuum.

22. A lens system as recited in claim 18, wherein said suction device is a device that creates a partial vacuum.

23. A lens system for contacting a cornea of an eye and holding the contacted cornea during a laser treatment, said system comprising:

a lens member having an anterior surface and formed with a contact surface opposed to said anterior surface, said contact surface shaped to contact the cornea;

a skirt, said skirt surrounding said contact surface and projecting outwardly therefrom to define a recessed chamber therebetween; and a plurality of projections, each said projection extending from said skirt for contact with the exterior surface of the eye, wherein said projections prevent the cornea from moving relative to said lens member.

24. A lens system as recited in claim 23 further comprising:

a means for mounting said lens member and said skirt to a laser system.

25. A lens system as recited in claim 23 further comprising:

a laser source for producing a laser beam, said laser source positioned to pass said laser beam through said lens member.

26. A device for contacting the anterior surface of a cornea of an eye for ophthalmic laser surgery which comprises:

an optical element having an anterior side and a posterior side, said posterior side being formed with a recessed chamber and having a contact surface and a sealing surface, such that the cornea is contacted against said contact surface when said sealing surface is pressed against the exterior surface of the eye, wherein said sealing surface is formed of a soft, medical grade plastic material that conforms to the exterior surface of the eye to establish a seal with the exterior surface of the eye when said sealing surface is pressed against the exterior surface of the eye.

27. A device as recited in claim 26 wherein said contact surface is substantially flat.

28. A device as recited in claim 26 wherein said contact surface is curved.

29. A device as recited in claim 26 wherein said sealing surface is concave extending into said recessed chamber.

30. A device as recited in claim 26 further comprising a retainer ring, said optical element being mounted on said retainer ring and further, wherein said retainer ring is attached to a laser system.

31. A device as recited in claim 26 wherein said contact surface is transparent.

32. A method for ophthalmic laser surgery which comprises the steps of:

providing a lens having a lens member, said lens member formed with an anterior surface and a contact surface, said contact surface being opposed to said anterior surface, said lens having a skirt surrounding said contact surface and extending outwardly therefrom to define a recessed chamber therebetween, said skirt having a sealing surface, such that a cornea is contacted against said contact surface when said sealing surface is pressed against the exterior surface of an eye, wherein said sealing surface is formed of a soft, medical grade plastic material that conforms to the exterior surface of the eye to establish a seal with the exterior surface of the eye when said sealing surface is pressed against the exterior surface of the eye;

placing said sealing surface of said skirt against the exterior surface of the eye;

pressing said sealing surface against the exterior surface of the eye, such that the cornea is contacted against the contact surface;

passing a laser beam through said anterior surface and said contact surface and into the cornea to perform ophthalmic laser surgery.

33. A method as recited in claim 32 wherein said contact surface is substantially flat.

34. A method as recited in claim 32 wherein said contact surface is curved.

35. A method as recited in claim 32 wherein said sealing surface is concave extending into said recessed chamber.

36. A method as recited in claim 32 wherein said contact surface is shaped to introduce less spherical aberration to said laser beam as said laser beam passes into the contacted cornea than is introduced into an identical laser beam passing into a cornea that is not contacted.

37. A method as recited in claim 32 wherein said lens member is transparent.

\* \* \* \* \*